(12) United States Patent
Niethammer

(10) Patent No.: US 8,280,492 B2
(45) Date of Patent: Oct. 2, 2012

(54) OPERATING METHOD OF AN X-RAY MACHINE FOR EXAMINING A PATIENT BY USE OF A CONTRAST AGENT

(75) Inventor: Matthias Niethammer, Möhrendorf (DE)

(73) Assignee: Siemens Aktiengesellschaft, Munich (DE)

( * ) Notice: Subject to any disclaimer, the term of this patent is extended or adjusted under 35 U.S.C. 154(b) by 1294 days.

(21) Appl. No.: 11/642,822

(22) Filed: Dec. 21, 2006

(65) Prior Publication Data

US 2007/0167750 A1 Jul. 19, 2007

(30) Foreign Application Priority Data

Dec. 23, 2005 (DE) .......................... 10 2005 061 850
Nov. 22, 2006 (DE) .......................... 10 2006 055 167

(51) Int. Cl.
*A61B 6/00* (2006.01)

(52) U.S. Cl. ................. 600/431; 600/425; 378/4; 705/3
(58) Field of Classification Search ............. 378/52–54, 378/4; 600/407, 425, 431; 705/3
See application file for complete search history.

(56) References Cited

U.S. PATENT DOCUMENTS

| | | | |
|---|---|---|---|
| 4,943,987 A | 7/1990 | Asahina et al. | |
| 5,396,418 A | 3/1995 | Heuscher | |
| 6,607,490 B2 * | 8/2003 | Ogasawara et al. | 600/458 |
| 6,745,066 B1 * | 6/2004 | Lin et al. | 600/425 |
| 7,821,261 B2 * | 10/2010 | Kimura | 324/307 |
| 8,023,707 B2 * | 9/2011 | Boese et al. | 382/128 |
| 2004/0223585 A1 * | 11/2004 | Heismann et al. | 378/54 |
| 2005/0185829 A1 * | 8/2005 | Heismann | 382/128 |
| 2009/0094058 A1 * | 4/2009 | Reiner | 705/3 |
| 2009/0257549 A1 * | 10/2009 | Heismann | 378/4 |
| 2010/0030073 A1 * | 2/2010 | Kalafut | 600/431 |

FOREIGN PATENT DOCUMENTS

| | | |
|---|---|---|
| DE | 38 26 550 C2 | 1/1994 |
| DE | 69417140 T2 | 9/1999 |

OTHER PUBLICATIONS

German Office Action, Oct. 24, 2006.

* cited by examiner

*Primary Examiner* — Brian Casler
*Assistant Examiner* — Amanda Lauritzen
(74) *Attorney, Agent, or Firm* — Harness, Dickey & Pierce, P.L.C.

(57) ABSTRACT

An operating method is disclosed for an X-ray machine for examining a patient by using a contrast agent in the case of which a preliminary examination is carried out for determining a contrast agent curve in the case of which a series of attenuation values relating to defined scanning instants are acquired at a set scanning position, the contrast agent curve being determined on the basis of the attenuation values, and being stored for a follow-up examination. The contrast agent curve can be loaded during a follow-up examination and need not be determined anew, and so a reduction is attained in the contrast agent used, the applied radiation dose and the examination time. The contrast agent curve can, furthermore, be adapted to the examination situation currently present by taking account of biosignals.

20 Claims, 2 Drawing Sheets

OPERATING METHOD OF AN X-RAY MACHINE FOR EXAMINING A PATIENT BY USE OF A CONTRAST AGENT

PRIORITY STATEMENT

The present application hereby claims priority under 35 U.S.C. §119 on German patent application numbers DE 10 2005 061 850.2 filed Dec. 23, 2005 and DE 10 2006 055 167.2 filed Nov. 22, 2006, the entire contents of each of which is hereby incorporated herein by reference.

FIELD

The Embodiments of the invention generally relate to a method for operating an X-ray machine for examining a patient by using a contrast agent.

BACKGROUND

The contrast in an X-ray image is usually caused by different attenuation properties of the substances relative to the X-radiation produced by an X-ray machine. When examining a patient, for example, it is possible on the basis of the different attenuation properties of bone tissue and soft part tissue to analyze the structure of the bone in the body interior of a patient on the basis of the contrast. Organs or vessels having an attenuation property similar to the surroundings cannot be examined in a conventional way because of too low a contrast.

For this reason, a contrast agent is used when examining an organ supplied with blood, for example, a heart or a liver. The contrast agent exhibits a different attenuation property by comparison with the surrounding tissue and so a visible contrast is produced between the organ and the surroundings in the image.

The propagation of the contrast agent in the patient's body is a highly dynamic process. After a certain time, the concentration of the contrast agent in an examination region being viewed rises steeply at first, reaches a maximum and subsequently falls back again. Thus, as the examination region is scanned at the concentration maximum, a preliminary examination with a small quantity of the contrast agent (test bolus) is firstly carried out at the beginning of each examination. The temporal behavior of the contrast agent concentration is represented in the form of a contrast agent curve on the basis of which the operating parameters of the X-ray machine are determined for carrying out the scanning. For example, the time suitable for starting the scanning can be calculated from the time interval between introducing the contrast agent and the observed maximum in the concentration.

If a further examination with the aid of a contrast agent is required for a patient at a later time, it is necessary, in turn, for an additional preliminary examination to be carried out with the aid of a test bolus in order to determine the operating parameters of the X-ray machine.

SUMMARY

In at least one embodiment of the present invention, a method is specified, with the aid of which the preconditions are set up such that follow-up examinations in which a contrast agent is used can be carried out with little outlay in conjunction with a reduced total radiation burden for a patient.

The inventor has found that during a follow-up examination the outlay on examination, and the dose of x-radiation applied to the patient can be substantially reduced when the information, obtained during a preliminary examination, for determining suitable operating parameters of the X-ray machine and/or the contrast agent device are made available for the follow-up examinations. It is thereby possible to dispense in follow-up examinations with carrying out a contrast agent measurement with the aid of a test bolus.

According to at least one embodiment of the invention, the operating method for an X-ray machine for examining a patient by using a contrast agent in the case of which a preliminary examination for determining a contrast agent curve is carried out includes the following method steps:

setting a scanning position,
carrying out a series of scans at predefined scanning instants, there being acquired in relation to each scan an attenuation value by means of which a concentration of the contrast agent at the scanning position is represented,
determining the contrast agent curve on the basis of the acquired attenuation values, and
storing the contrast agent curve for a later follow-up examination of the patient.

The contrast agent curve in this case specifies the relationship between the concentration of the contrast agent at the scanning location and time. The curve can be stored in parameterized form, for example in the form of coefficients of a higher-order polynomial representing the curve.

Suitable operating parameters for future follow-up examinations can be determined from the stored contrast agent curve. The preliminary examination with the aid of a test bolus is therefore to be carried out only once and is eliminated in all follow-up examinations. For the follow-up examination, this elimination results in a time saving for the entire examination period, a reduction in the overall applied X-ray dose, and a saving in contrast agent.

Together with the contrast agent curve, the injection parameters, set during the preliminary examination, of the contrast agent device are advantageously also stored. It would also be conceivable that a contrast agent protocol used in the preliminary examination also be stored instead of the individual injection parameters. With the aid of the contrast agent protocol, it is usually possible to define different preliminary examination phases that run sequentially in time and in the case of which the injection parameters have different values.

Particularly suitable operating parameters can be calculated both for the X-ray machine and for the contrast agent device for an imminent follow-up examination from the stored contrast agent curve in conjunction with the stored injection parameters and/or in conjunction with the stored contrast agent protocol. The information relating to the injection parameters and/or to the contrast agent protocol are required, in particular, when the preliminary examination has not be carried out with preset standard values for the injection parameters. Injection parameters advantageously comprise a flow rate in units of ml/s, and/or an injected volume of the contrast agent in units of ml and/or an injection period in units of seconds.

According to an advantageous refinement of at least one embodiment of the invention, the contrast agent curve is stored together with the patient's acquired biosignals. It is stored therefore also possible to specify at a later time under which physiological boundary conditions the contrast agent curve was recorded. The contrast agent curve can, furthermore, be normalized with regard to at least one acquired biosignal so that it is possible to intercompare contrast agent curves of various patients.

Moreover, it is also possible from a comparison of the stored biosignals with the acquired biosignals at the time of the follow-up examination in the event of repeated examinations of a patient to adapt the contrast agent curve to the situation currently present.

An adaptation of the contrast agent curve is apposite for easily accessible biosignals, in particular. The biosignals therefore preferably include a patient's heart rate which can easily be determined with the aid of a conventional pulse meter. For example, given a higher heart rate at the time of the follow-up examination, the contrast agent curve can be adapted by compressing the curve appropriately. The converse holds given a low acquired heart rate. By neglecting physiological parameters affecting the contrast agent curve, which are present in the event of a change in heart rate, it is possible to perform an adaptation in the simplest case by linearly compressing or stretching the contrast agent curve as a function of the heart rate. However, the biosignals can likewise advantageously comprise the patient's blood pressure. It is also possible to determine the blood pressure easily by means of a conventional blood pressure meter, and the blood pressure can be used in a way comparable to the heart rate for the purpose of adapting the contrast agent curve.

Furthermore, it is advantageously possible to use as biosignal an ejection fraction of the patient's heart, advantageously for adapting the curve. The ejection fraction corresponds to the quantity of blood that is ejected from the left-hand ventricle of the heart with each heart beat. It is calculated from the diastolic and systolic volumes in accordance with the following equation:

$$EF=(EDV-ESV)/EDV, \text{where}$$

EF represents the ejection fraction,
EDV represents the diastolic volume, and
ESV represents the systolic volume.

The diastolic and systolic volumes can be determined in a simple way with the aid of echocardiography.

According to a further advantageous refinement of at least one embodiment of the invention, the contrast agent curve can be stored together with data on the patient's age and/or weight, the point being that given an increase or decrease in the weight and/or an increase in the age of the patient, it can likewise be necessary to adapt the contrast agent curve. The relationship between age, weight and the contrast agent curve can, for example, be calculated on the basis of a database that can be continually expanded and in which a multiplicity of contrast agent curves of different patients are entered.

A reliable access to, and a simple management of the contrast agent curve are advantageously ensured whenever the contrast agent curve is stored together with an electronic patient file. The operating parameters of the X-ray machine for carrying out the examination of the patient can be calculated in a simple way by evaluating the contrast agent curve.

The operating parameters include a delay time measured relative to the beginning of the examination, for beginning the scanning of the patient. In the simplest case, the delay time is determined from the contrast agent curve by determining the instant at which the curve exhibits its local maximum. The local maximum of the curve corresponds here to the maximum concentration of the contrast agent at the location of the scanning position.

The operating parameters are preferably stored together with the contrast agent curve. In the case where there is no need to adapt the contrast agent curve, the operating parameters are directly available during a follow-up examination, without the need for recalculation.

In the case of an adaptation or a correction of the contrast agent curve, corrected operating parameters can advantageously be calculated, and so adding contrast agent and scanning the follow-up examination are tuned to one another.

BRIEF DESCRIPTION OF THE DRAWINGS

Example embodiments of the invention and further advantageous refinements of the invention are disclosed and illustrated in the following schematics, in which.

DETAILED DESCRIPTION OF THE EXAMPLE EMBODIMENTS

Figure 1:
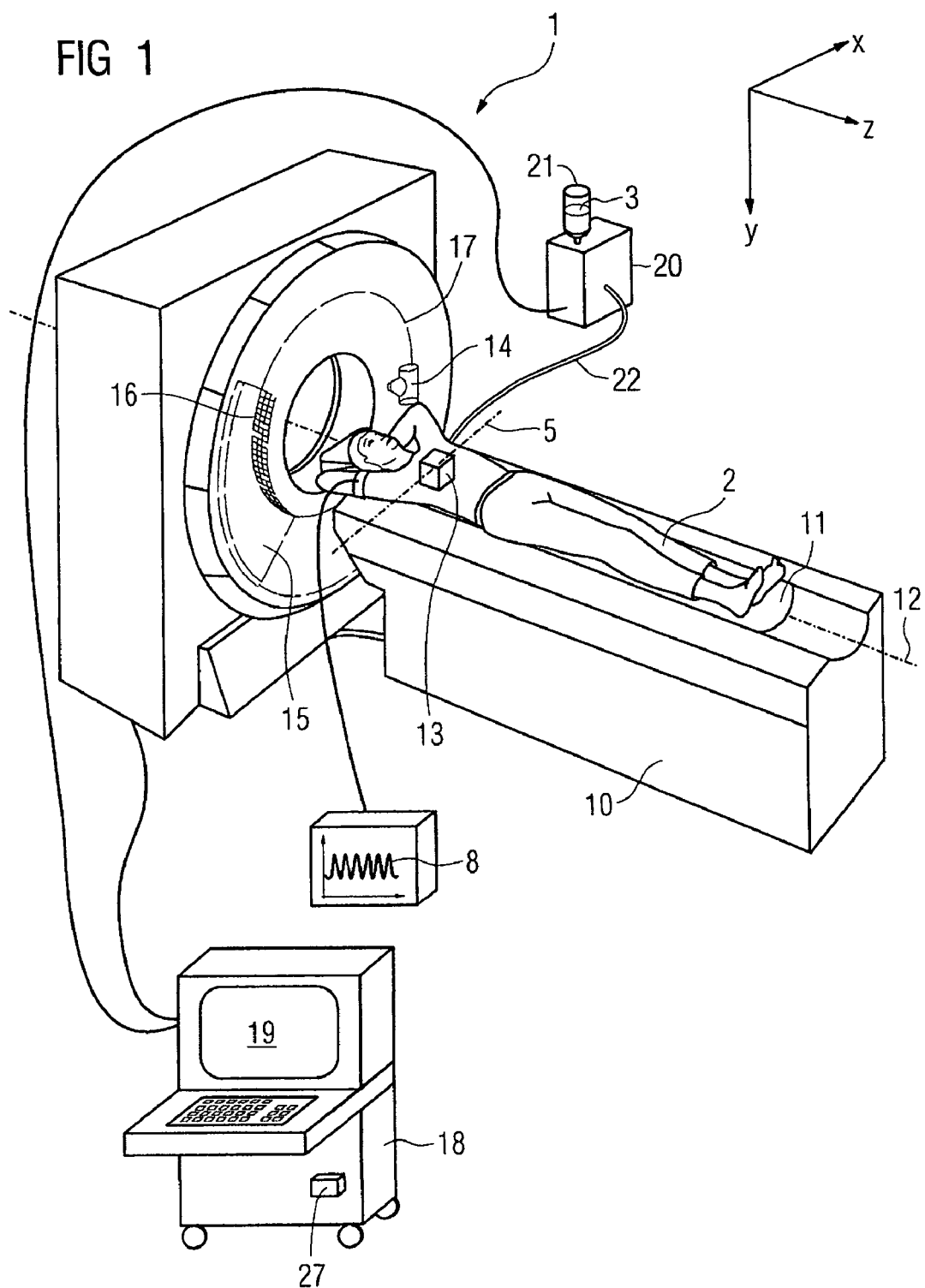
FIG. 1 shows a perspective illustration of a computed tomography unit that is suitable for carrying out the inventive operating method for examining a patient by using a contrast agent.

The terminology used herein is for the purpose of describing particular embodiments only and is not intended to be limiting of the present invention. As used herein, the singular forms "a", "an" and "the" are intended to include the plural forms as well, unless the context clearly indicates otherwise. It will be further understood that the terms "includes" and/or "including", when used in this specification, specify the presence of stated features, integers, steps, operations, elements, and/or components, but do not preclude the presence or addition of one or more other features, integers, steps, operations, elements, components, and/or groups thereof.

In describing example embodiments illustrated in the drawings, specific terminology is employed for the sake of clarity. However, the disclosure of this patent specification is not intended to be limited to the specific terminology so selected and it is to be understood that each specific element includes all technical equivalents that operate in a similar manner.

Referencing the drawings, wherein like reference numerals designate identical or corresponding parts throughout the several views, example embodiments of the present patent application are hereafter described.

Shown in a perspective view in FIG. 1 is an X-ray machine, here a computed tomography unit provided with the reference numeral 1, that is suitable for carrying out the inventive operating method for examining a patient 2 while using a contrast agent 3.

The computed tomography unit 1 is assigned a bearing apparatus 10 with a movable table plate 11 on which the patient 2 can be borne. The table plate 11 can be adjusted in the direction of the axis of rotation 12 such that an examination region 13 associated with the patient 2 can be moved into the measuring range of a recording system 14, 15 through an opening in the housing of the computer tomograph 1. The patient 2 and the recording system 14, 15 can in this way be adjusted relative to one another in the direction of the axis of rotation 12 such that different scanning positions can be adopted.

In order to acquire projections, the recording system 14, 15 has an emitter 14 in the form of an X-ray tube, and a detector 15 arranged opposite the latter, the detector 15 being of arcuate design and comprising a number of detector elements 16 lined up to form detector rows. The emitter 14 generates radiation in the form of a fan-shaped X-ray beam that penetrates the measuring region and subsequently strikes the detector elements 16 of the detector 15. The detector elements 16 produce an attenuation value 7 depending on the attenuation of the X-radiation passing through the measuring region. The conversion of the X-radiation into an attenuation value 7 is performed in each case, for example, by means of a photodiode optically coupled to a scintillator, or by means of a directly converting semiconductor. The detector 15 in this way produces a set of attenuation values 7 that is also denoted as a projection.

The recording system 14, 15 is arranged rotatably on a gantry 17 such that projections can be acquired from different projection directions. Depending on the operating mode set for the computed tomography unit 1, the scanning is performed with a permanently set or variable projection direction in conjunction with a permanently set or variable scanning position.

By way of example, projections from a multiplicity of different projection directions at various positions along the axis of rotation 12 or along the patient 2 are acquired by rotating the gantry 17 while simultaneously continuously advancing the patient 2 in the direction of the axis of rotation 12. The projections of the recording system 14, 15 that are obtained in this way by spiral scanning are transmitted to an arithmetic logic unit 18 and converted to an image that can be displayed on a display unit 19. The image can be, for example, a slice image or volume image of an examination region 13.

In order to examine organs supplied with blood, for example a heart or a liver or a vessel, the patient 2 can be injected if required with a contrast agent 3 by means of a contrast agent device 20 in order to increase the visible contrast against the surrounding soft part tissue. The contrast agent 3 is pumped in an automated and time-controlled fashion from a supply container 21 via a contrast agent tube 22 in an adjustable amount and at an adjustable flow rate into a vein of the patient 2. The parameters for the administration of contrast agent can be prescribed by the arithmetic unit 18 by means of an electrical connection between the arithmetic unit 18 and the contrast agent device 20.

The propagation of the contrast agent 3 in the interior of the body is a highly dynamic process. The introduced contrast agent 3 traverses the blood circulation of the patient 2, not reaching the examination region 13 until after a certain time. Once the examination region 13 has been reached, the concentration of the contrast agent 3 firstly rises steeply, reaches a maximum and subsequently falls off again. The temporal behavior of the concentration can be represented in the form of a contrast agent curve 4.

Suitable operating parameters of the computed tomography unit 1 are determined on the basis of this contrast agent curve 4, and so the scanning is performed at a time and rate when the concentration of the contrast agent 3 in the examination region 13 is as high as possible. The operating parameters essentially comprise a starting instant of the scanning and the scanning rate as well as the pitch value, that is to say the ratio between the advance of the table plate 11 per gantry rotation and the slice thickness of the detector 15.

Figure 2:
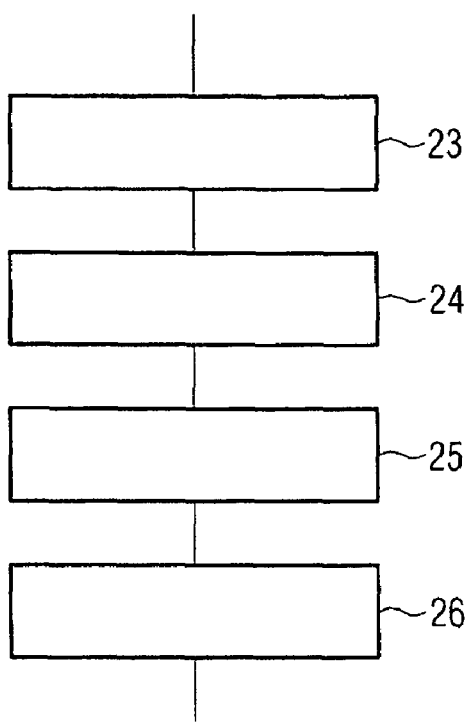
FIG. 2 shows the operating method for examining the patient.

The determination of the contrast agent curve 4 is performed in conjunction with a preliminary examination, and essentially comprises the method steps shown in FIG. 2:

First Step 23:
Setting a fixed scanning position 5 and a fixed projection direction.

Second Step 24:
Carrying out a series of scans at predefined scanning instants 6, there being acquired in relation to each scan, an attenuation value 7 by means of which a concentration of the contrast agent 3 at the scanning position 5 is represented.

Third Step 25:
Determining the contrast agent curve 4 on the basis of the acquired attenuation values 7.

Fourth Step 26:
Storing the contrast agent curve 4 for a later follow-up examination of the patient 2.

Figure 3:
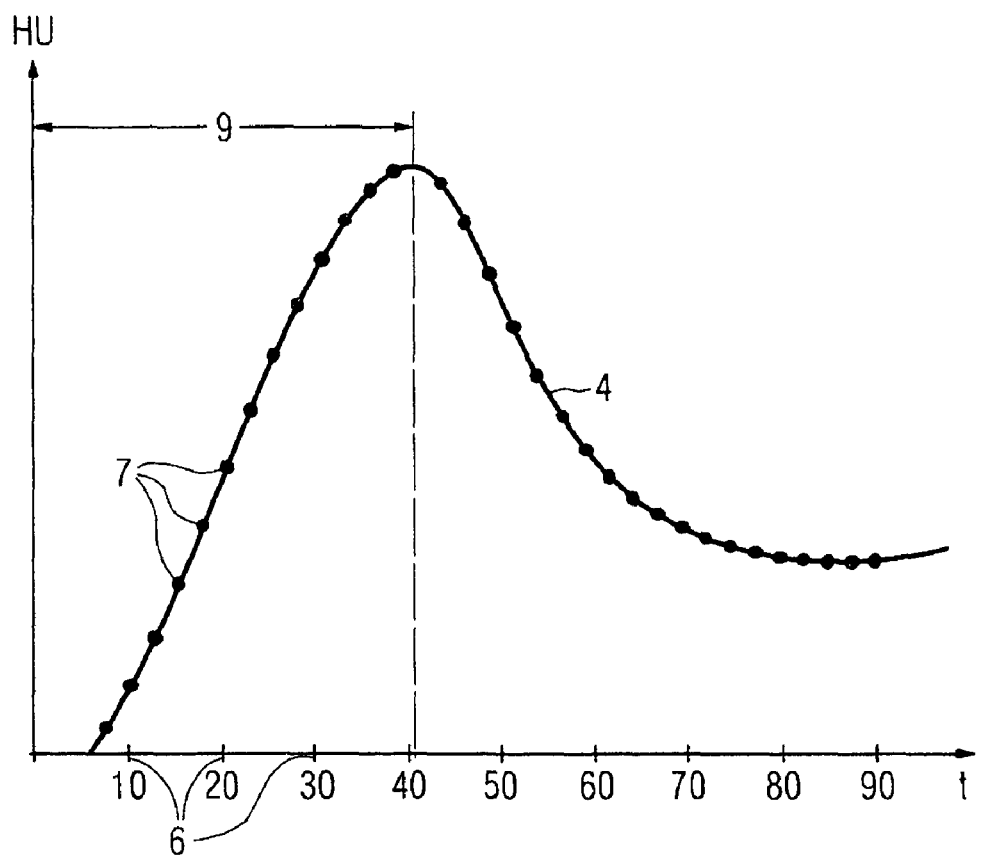
FIG. 3 shows a contrast agent curve that was determined during a preliminary examination.

A contrast agent curve 4 is illustrated by way of example, in FIG. 3. Time in units of second(s) is plotted along the x-axis. The y-axis corresponds to the relative attenuation values in Hounsfield units (HU). Attenuation values 7 were acquired every 2 seconds in the example. For reasons of clarity, not all the attenuation values 7 and not all the scanning instants 6 have been provided with a reference numeral. The attenuation values 7 have been plotted as points in the diagram and serve for calculating the contrast agent curve 4.

The contrast agent curve 4 runs through the measuring points and produces a continuous relationship between time and attenuation at the location of the scanning. The curve can be represented as a function, for example, in the form of a higher-order polynomial. The coefficients of the polynomial can be determined from the measuring points using an approximation method known per se. In this case, when storing the contrast agent curve it is necessary merely to store the coefficients and not the individual attenuation values 7, and this leads to a reduction in the storage space required.

The scanning position 5 in the preliminary examination is selected as a rule such that scanning is carried out directly in front of or inside the examination region 13 such that the contrast agent curve 4 directly reproduces the change in the contrast agent concentration at the location of a subsequent examination. The scanning positions of the preliminary examination and of the follow-up examination need not necessarily coincide. Generalized parameters by which the dynamics of the blood circulation are described can be determined from the known positional relationship between the location of the contrast agent administration and the scanning position. The operating parameters for a follow-up examination at the very different scanning positions of the patient 2 can be determined on the basis of such parameters.

The storage of the contrast agent curve 4 is performed together with injection parameters of the contrast agent device 20 set during the preliminary examination. This is required, in particular whenever no standard values have been used for the injection parameters in the preliminary examination. An interpretation of the contrast agent curve 4, and a calculation of suitable operating parameters for the X-ray machine 1 and/or for the contrast agent device 20 are possible for a follow-up examination only when the information relating to the injection parameters used in the preliminary examination are to hand.

Instead of the individual injection parameters, it would also be conceivable to store a contrast agent protocol used in the preliminary examination, and to use it when calculating the operating parameters. It is usually possible to define, with the aid of the contrast agent protocol, different preliminary examination phases that run consecutively in time and in the case of which the injection parameters have different values. The injection parameters include, for example, a flow rate in units of ml/s and/or an injected volume of the contrast agent in units of ml and/or an injection period in units of seconds.

During the preliminary examination, a signaling apparatus acquires not only the attenuation values 7 required for determining the contrast agent curve 4, but also different biosignals 8 such as, for example, heart rate, blood pressure, ejection fraction and number of heart beats. Such biosignals 8 influence the course of the curve and can be used to adapt or correct the contrast agent examination during an examination to be carried out later.

The storage of the contrast agent curve 4 is performed together with the acquired biosignals 8 of the patient and together with an electronic patient file in a database 27 assigned to the arithmetic unit 18. The electronic patient file can, moreover, include yet further information that is evaluated before an examination and updated after each examination. Thus, for example, it is possible to store whether the contrast agent 3 has arrived at the correct instant, too early, too late or in too diluted a fashion in the examination region 13.

The scanning can be corrected additionally by evaluating this information. On the basis of the information logged from past examinations, it is, for example possible to perform the scanning at an earlier instant than calculated for the case when the contrast agent 3 always enters the examination region 13 prematurely. Conversely, an additional delay in scanning can be sensible whenever the contrast agent 3 always enters the examination region 13 too late. The information logged therefore serves to assure the quality of the examination.

The contrast agent curve 4 can be loaded from the database 27 during a follow-up examination of the patient 2 that is undertaken at a later time, and does not need to be determined anew. Owing to the omission of a corresponding preliminary examination, the examination time and the applied X-radiation are reduced. Moreover, expensive contrast agent which damages health is saved.

The stored biosignals and the biosignals newly acquired in relation to the follow-up examination serve for adapting the contrast agent curve 4 to the current situation. In the simplest case, the curve can be compressed or stretched for the purpose of adaptation as a function of the difference in the biosignals, for example, the difference in the two heart rates, the blood pressures, the number of heart beats, or the ejection fractions.

A linear compression or stretching is permissible as coarse correction whenever it is to be assumed that the blood flow rate at the location of the examination behaves linearly in relation to the difference in the biosignal considered. A nonlinear relationship between the adaptation and the biosignals can be determined by a study in which the results from the preliminary examinations of very many different patients 2 are evaluated.

The operating parameters of the computed tomography unit 1 required for the examination can be calculated from the contrast agent curve 4 thus corrected. The delay time 9 may be mentioned by way of example. The delay time 9 between the contrast agent administration and start of the scanning results from the position of the local maximum in the contrast agent curve 4. During the examination of a volume, in the case of which projections must be acquired from a plurality of rotations of the recording system 14, 15, it can be necessary, moreover, for the contrast agent 3 to have a high concentration over a lengthy period within the examination region 13. The amount of the contrast agent 3 can also depend in this situation on the gradient of the curve after the maximum is achieved. In the event of a slight drop in the curve, or of a slight negative gradient, the amount of the contrast agent 3 supplied can be correspondingly reduced.

An idea of at least one embodiment of the invention can be summarized as follows:

At least one embodiment of the invention relates to an operating method for an X-ray machine 1 for examining a patient 2 by using a contrast agent 3 in the case of which a preliminary examination is carried out for determining a contrast agent curve 4 in the case of which a series of attenuation values 7 relating to defined scanning instants 6 are acquired at a set scanning position 5, the contrast agent curve 4 being determined on the basis of the attenuation values 7, and being stored for a follow-up examination. The contrast agent curve 4 can be loaded during a follow-up examination and need not be determined anew, and so a reduction is attained in the contrast agent used, the applied radiation dose and the examination time. The contrast agent curve 4 can, furthermore, be adapted to the examination situation currently present by taking account of biosignals 8.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. An operating method for an X-ray machine for examining a patient by using a contrast agent, a preliminary examination method for determining a contrast agent curve being carried out according to the method comprising:
setting a scanning position;
carrying out a series of scans at defined scanning instants, there being acquired in relation to each scan an attenuation value by which a concentration of the contrast agent at the scanning position is represented;
determining the contrast agent curve with respect to time on the basis of the acquired attenuation values;
storing the determined contrast agent curve for a later follow-up examination of the patient; and
accessing the contrast agent curve from the preliminary examination during the follow-up examination.

2. The method as claimed in claim 1, wherein the contrast agent curve is stored together with injection parameters from the preliminary examination.

3. The method as claimed in claim 2, wherein the injection parameters include at least one of a flow rate, an injected volume and an injection period of the contrast agent.

4. The method as claimed in claim 1, wherein the contrast agent curve is stored together with acquired biosignals of the patient.

5. The method as claimed in claim 4, wherein the biosignals include a heart rate of the patient.

6. The method as claimed in claim 4, wherein the biosignals include a blood pressure of the patient.

7. The method as claimed in claim 4, wherein the biosignals include an ejection fraction of a heart of the patient.

8. The method as claimed in claim 4, wherein the biosignals include a number of the heartbeats of the patient.

9. The method as claimed in claim 1, wherein the contrast agent curve is stored together with data on at least one of age and weight of the patient.

10. The method as claimed in claim 1, wherein the contrast agent curve is stored together with an electronic patient file.

11. The method as claimed in claim 1, wherein at least the stored contrast agent curve is loaded during the follow-up examination.

12. The method as claimed in claim 2, wherein the contrast agent curve is stored together with acquired biosignals of the patient.

13. The method as claimed in claim 3, wherein the contrast agent curve is stored together with acquired biosignals of the patient.

14. The method as claimed in claim 5, wherein the biosignals include a blood pressure of the patient.

15. An operating method for an X-ray machine for examining a patient by using a contrast agent, a preliminary examination for determining a contrast agent curve being carried out according to the method comprising:
   setting a scanning position;
   carrying out a series of scans at defined scanning instants, there being acquired in relation to each scan an attenuation value by which a concentration of the contrast agent at the scanning position is represented;
   determining the contrast agent curve with respect to time on the basis of the acquired attenuation values; and
   storing the determined contrast agent curve for a later follow-up examination of the patient, wherein operating parameters of the X-ray machine for carrying out the examination of the patient are calculated by evaluating the contrast agent curve.

16. The method as claimed in claim 15, wherein the operating parameters include a delay time measured relative to the beginning of the examination, for beginning the scanning of the patient.

17. The method as claimed in claim 15, wherein the operating parameters are stored together with the contrast agent curve.

18. The method as claimed in claim 16, wherein the operating parameters are stored together with the contrast agent curve.

19. An operating method for an X-ray machine for examining a patient by using a contrast agent, a preliminary examination for determining a contrast agent curve being carried out according to the method comprising:
   setting a scanning position;
   carrying out a series of scans at defined scanning instants, there being acquired in relation to each scan an attenuation value by which a concentration of the contrast agent at the scanning position is represented;
   determining the contrast agent curve with respect to time on the basis of the acquired attenuation values; and
   storing the determined contrast agent curve for a later follow-up examination of the patient, wherein at least the stored contrast agent curve is loaded during the follow-up examination and the contrast agent curve is corrected as a function of the biosignals of the patient acquired at the time of the follow-up examination.

20. The method as claimed in claim 19, wherein corrected operating parameters are calculated from the corrected contrast agent curve.

* * * * *

UNITED STATES PATENT AND TRADEMARK OFFICE
CERTIFICATE OF CORRECTION

PATENT NO. : 8,280,492 B2
APPLICATION NO. : 11/642822
DATED : October 2, 2012
INVENTOR(S) : Niethammer Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1420 days.

Signed and Sealed this
Twenty-third Day of September, 2014

Michelle K. Lee
*Deputy Director of the United States Patent and Trademark Office*